(12) United States Patent
Golberg et al.

(10) Patent No.: US 10,054,551 B2
(45) Date of Patent: Aug. 21, 2018

(54) INSPECTION SYSTEM AND METHOD FOR INSPECTING A SAMPLE BY USING A PLURALITY OF SPACED APART BEAMS

(71) Applicant: APPLIED MATERIALS ISRAEL LTD., Rehovot (IL)

(72) Inventors: Boris Golberg, Ashdod (IL); Ron Naftali, Shoham (IL)

(73) Assignee: Applied Materials Israel Ltd., Rehovot (IL)

( * ) Notice: Subject to any disclaimer, the term of this patent is extended or adjusted under 35 U.S.C. 154(b) by 292 days.

(21) Appl. No.: 15/134,278

(22) Filed: Apr. 20, 2016

(65) Prior Publication Data
US 2017/0307539 A1    Oct. 26, 2017

(51) Int. Cl.
*G01N 21/88* (2006.01)
(52) U.S. Cl.
CPC ... *G01N 21/8851* (2013.01); *G01N 2201/063* (2013.01); *G01N 2201/105* (2013.01)
(58) Field of Classification Search
CPC ........... G01N 21/8851; G01N 21/9505; G01N 21/9501; G01N 21/956
(Continued)

(56) References Cited

U.S. PATENT DOCUMENTS 5,502,306 A  3/1996 Meisburger et al.
5,869,833 A  2/1999 Richardson et al.
(Continued)

FOREIGN PATENT DOCUMENTS

JP  2000215834 A  8/2000
JP  2009507352 A  2/2009
(Continued)

OTHER PUBLICATIONS

U.S. Appl. No. 14/795,793, "First Action Interview Pilot Program Pre-Interview Communication", dated May 11, 2017, 4 pages.
(Continued)

*Primary Examiner* — Que T Le
(74) *Attorney, Agent, or Firm* — Kilpatrick Townsend & Stockton LLP (57) ABSTRACT

An inspection system that may include an illumination module that may be configured to scan a sample during multiple scan iterations; wherein during each scan iteration the illumination module scans each beam of a plurality of spaced apart beams along a scan line; a mechanical stage that may be configured to move the sample during the multiple scan iterations; a detection module; and a processor; wherein when the inspection system operates in an interlaced mode, the mechanical stage may be configured to move at a first speed thereby preventing a substantial overlap between scan lines obtained during the multiple scan iterations; wherein when the inspection system operates in a non-interlaced mode: the mechanical stage may be configured to move at a second speed that differs from the first speed thereby introducing an overlap between scan lines of different beams that may be obtained during different scan iterations; the detection module may be configured to generate detection signals in response to a detection of radiation emitted from the sample as a result of each scan line; and wherein the processor may be configured to independently process detection signals relating to different scan lines.

12 Claims, 8 Drawing Sheets

(58) Field of Classification Search
USPC .............................................. 250/559.4, 221
See application file for complete search history.

(56) References Cited

U.S. PATENT DOCUMENTS

| | | | |
|---|---|---|---|
| 6,570,155 | B1 | 5/2003 | Prior et al. |
| 6,759,655 | B2 | 7/2004 | Nara et al. |
| 7,095,022 | B2 | 8/2006 | Nakasuji et al. |
| 7,253,410 | B1 | 8/2007 | Bertsche et al. |
| 7,253,645 | B2 | 8/2007 | Talbot et al. |
| 7,897,942 | B1 | 3/2011 | Bareket et al. |
| 7,940,384 | B2 * | 5/2011 | Hill .................... G01N 21/9501 356/237.3 |
| 7,994,476 | B2 | 8/2011 | Bullock et al. |
| 8,063,363 | B2 | 11/2011 | Yeh et al. |
| 8,378,320 | B2 | 2/2013 | Platzgummer |
| 8,497,475 | B2 | 7/2013 | Yeh et al. |
| 8,884,224 | B2 | 11/2014 | Jau et al. |
| 2005/0279936 | A1 | 12/2005 | Litman et al. |
| 2006/0245636 | A1 | 11/2006 | Kitamura et al. |
| 2008/0122462 | A1 | 5/2008 | Nozoe et al. |
| 2008/0277598 | A1 | 11/2008 | Satoh et al. |
| 2009/0050802 | A1 | 2/2009 | Noji et al. |
| 2009/0134340 | A1 | 5/2009 | Furuhashi et al. |
| 2009/0242761 | A1 | 10/2009 | Yeh et al. |
| 2009/0256075 | A1 | 10/2009 | Kemen et al. |
| 2010/0072365 | A1 | 3/2010 | Shoham et al. |
| 2011/0181688 | A1 | 7/2011 | Miyamoto et al. |
| 2012/0305768 | A1 | 12/2012 | Yamamoto et al. |
| 2015/0200071 | A1 | 7/2015 | Sender et al. |
| 2015/0311031 | A1 | 10/2015 | Platzgummer et al. |
| 2016/0322195 | A1 | 11/2016 | Sender et al. |
| 2017/0011883 | A1 | 1/2017 | Lev et al. |

FOREIGN PATENT DOCUMENTS

| | | |
|---|---|---|
| JP | 4997076 A | 6/2009 |
| JP | 2017504175 A | 2/2017 |
| KR | 1020080087138 A | 9/2008 |
| KR | 10-1751663 B1 | 6/2017 |
| TW | 201106411 A | 2/2011 |
| TW | 201237443 A | 9/2012 |
| WO | 2015106212 A1 | 7/2015 |

OTHER PUBLICATIONS

TW104101097, "Office Action", dated May 24, 2017, 4 pages.
Notice of Allowance for related U.S. Appl. No. 15/207,024 dated Jul. 14, 2017, 13 pages.
First Action Interview Office Action Summary for related U.S. Appl. No. 14/795,793 dated Aug. 7, 2017, 4 pages.
Decision of Patent Examination by Intellectual Property Office Ministry of Economic Affairs for related Taiwanese Patent Application No. 104101097 dated Aug. 15, 2017, 4 pages.
U.S. Appl. No. 14/795,793, "Final Office Action", dated Oct. 4, 2017, 9 pages.
U.S. Appl. No. 14/795,793, "Advisory Action", dated Jan. 11, 2018, 5 pages.
U.S. Appl. No. 14/153,923, "Final Office Action", dated Apr. 19, 2016, 8 pages.
U.S. Appl. No. 14/153,923, "Non-Final Office Action", dated Sep. 2, 2015, 9 pages.
U.S. Appl. No. 14/153,923, "Notice of Allowance", dated Jul. 20, 2016, 5 pages.
U.S. Appl. No. 14/795,793, "Restriction Requirement", dated Feb. 16, 2017, 6 pages.
KR10-2016-7021872, "Notice of Decision to Grant", dated Mar. 21, 2017, 2 pages.
PCT/US2015/011050, "International Preliminary Report on Patentability", dated Jul. 28, 2016, 9 pages.
PCT/US2015/011050, "International Search Report and Written Opinion", dated Apr. 29, 2015, 12 pages.

* cited by examiner

INSPECTION SYSTEM AND METHOD FOR INSPECTING A SAMPLE BY USING A PLURALITY OF SPACED APART BEAMS

BACKGROUND

Samples such as but not limited to wafers may have a variety of defects of microscopic and nanometric scale of different shapes, sizes and materials.

An inspection condition that may be used for detecting one defect may not be adequate for detecting another defect.

There is a growing need to provide an inspection system that may detect defects of different types.

SUMMARY

According to an embodiment of the invention there may be provided an inspection system that may include an illumination module that may be configured to scan a sample during multiple scan iterations; wherein during each scan iteration the illumination module scans each beam of a plurality of spaced apart beams along a scan line; a mechanical stage that may be configured to move the sample during the multiple scan iterations; a detection module; and a processor; wherein when the inspection system operates in an interlaced mode, the mechanical stage may be configured to move at a first speed thereby preventing a substantial overlap between scan lines obtained during the multiple scan iterations; wherein when the inspection system operates in a non-interlaced mode: the mechanical stage may be configured to move at a second speed that differs from the first speed thereby introducing an overlap between scan lines of different beams that may be obtained during different scan iterations; the detection module may be configured to generate detection signals in response to a detection of radiation emitted from the sample as a result of each scan line; and wherein the processor may be configured to independently process detection signals relating to different scan lines.

When the inspection system operates in a non-interlaced mode the illumination module may be configured to introduce a difference between at least one optical property of at least two of the plurality of spaced apart beams.

The at least one optical property may differ from an angle of incidence of the at least two of the plurality of spaced apart beams.

The at least one optical property may be a polarization of the at least two of the plurality of spaced apart beams.

The illumination module may include a scanner and beam splitter for generating the plurality of spaced apart beams and for scanning the plurality of spaced apart beams.

The illumination module may include a first pair of relay lenses followed by an aperture stop; and wherein the aperture stop may be followed by a three relay lenses and a beam splitter.

According to an embodiment of the invention there may be provided an inspection system that may include an illumination module that may be configured to scan a sample during multiple scan iterations; wherein during each scan iteration the illumination module scans each beam of a plurality of spaced apart beams along a scan line; a mechanical stage that may be configured to move the sample during the multiple scan iterations; a detection module; and a processor; wherein when the inspection system operates in a non-interlaced mode: the mechanical stage may be configured to move the sample and introduce an overlap between scan lines of different beams that may be obtained during different scan iterations; the illumination module may be configured to introduce a difference between at least one optical property of at least two of the plurality of spaced apart beams; wherein the at least one optical property differs from an angle of incidence on the sample; the detection module may be configured to generate detection signals in response to a detection of radiation emitted from the sample as a result of each scan line; and wherein the processor may be configured to independently process detection signals relating to different scan lines.

The at least one optical property may be a polarization of the at least two of the plurality of spaced apart beams.

The at least one optical property may differ from an angle of incidence of the at least two of the plurality of spaced apart beams.

The illumination module may include a scanner and beam splitter for generating the plurality of spaced apart beams and for scanning the plurality of spaced apart beams.

The inspection illumination module may include a first pair of relay lenses followed by an aperture stop; and wherein the aperture stop may be followed by three relay lenses and a beam splitter.

According to an embodiment of the invention there may be provided a method that may include scanning the sample by an illumination module of an inspection system during multiple scan iterations; wherein during each scan iteration the illumination module scans each beam of the plurality of spaced apart beams along a scan line; moving the sample, by a mechanical stage of the inspection system, during the multiple scan iterations; detecting, by a detection module of the inspection system, radiation emitted from the sample as a result of each scan line and generating detection signals in response to the detecting of the radiation; and independently processing, by a processor of the inspection system, detection signals relating to different scan lines; wherein when the inspection system operates in an interlaced mode, the moving of the sample may be done at a first speed thereby preventing a substantial overlap between scan lines obtained during the multiple scan iterations; and wherein when the inspection system operates in a non-interlaced mode, the moving of the sample may be done at a second speed that differs from the first speed thereby introducing an overlap between scan lines of different beams that may be obtained during different scan iterations.

BRIEF DESCRIPTION OF THE DRAWINGS

The subject matter regarded as the invention is particularly pointed out and distinctly claimed in the concluding portion of the specification. The invention, however, both as to organization and method of step, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Figure 1:
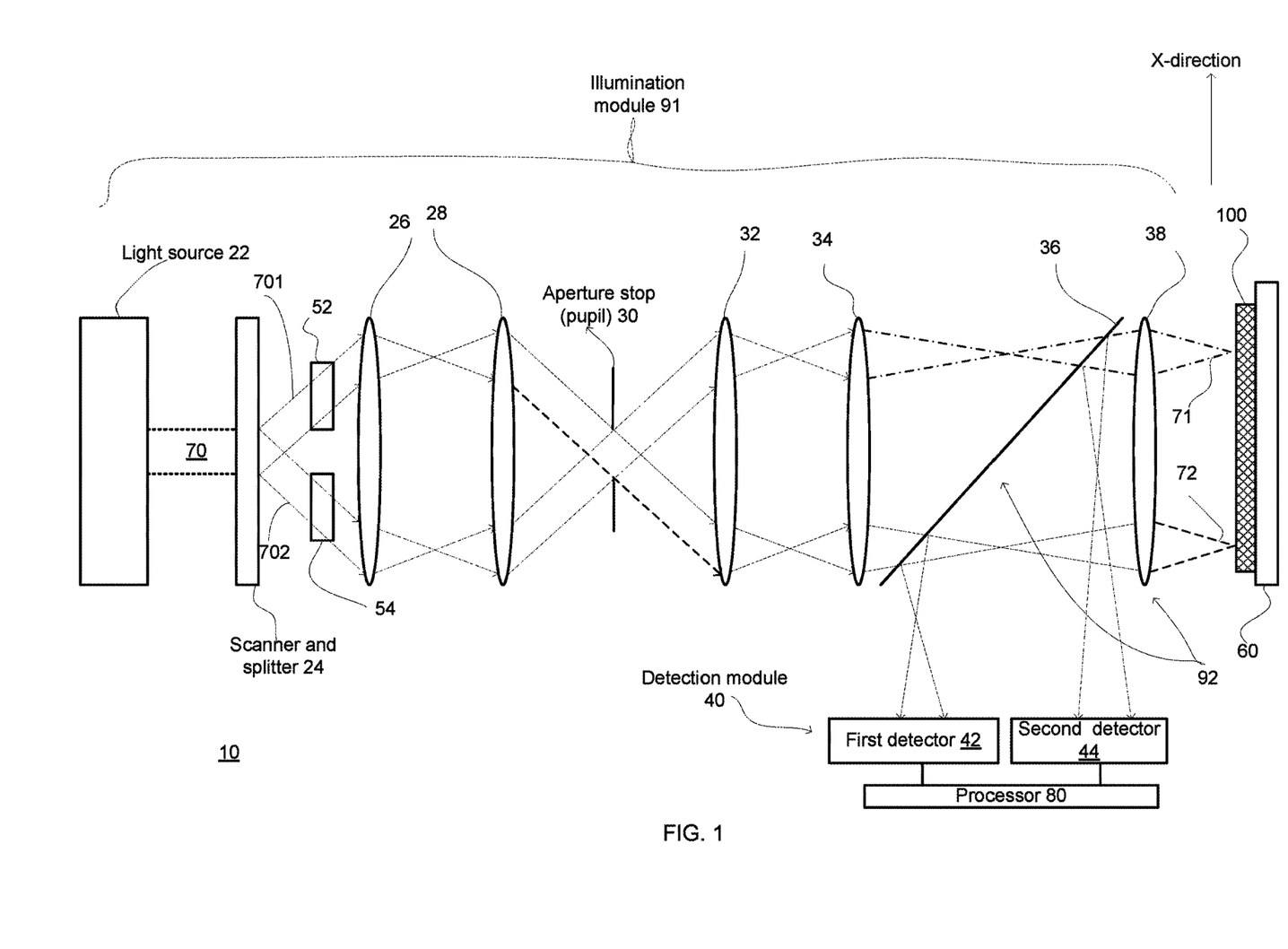
FIG. 1 illustrates a sample and an inspection system according to an embodiment of the invention.

FIG. 1 illustrates inspection system 10 and sample 100 according to an embodiment of the invention.

Inspection system 10 includes illumination module 91, mechanical stage 60, detection module 40, processor 80 and collection module 92.

Illumination module 91 is configured to scan a sample 100 during multiple scan iterations. During each scan iteration the illumination module 91 scans each beam of a plurality of spaced apart beams (such as beams 71 and 72) along a scan line.

Mechanical stage 60 is configured to move the sample during the multiple scan iterations.

According to an embodiment of the invention, inspection system 10 may operate in multiple modes such as an interlaced mode and a non-interlaced mode. The inspection system 10 may operate in more than these two modes. Alternatively, the inspection system 10 may operate only in a non-interlaced mode.

When the inspection system operates in an interlaced mode, the mechanical stage is configured to move at a first speed thereby preventing a substantial overlap between scan lines obtained during the multiple scan iterations.

In this mode there may be a non-substantial overlap between scan lines. The non-substantial overlap means up to 5% or 10% percent overlap. The non-substantial overlap may be provided in order to prevent gaps in the coverage of the sample. A non-substantial overlap may be introduced in order to compensate for inaccuracies in the mechanical movement of the mechanical stage 60 and/or compensate for light scan inaccuracies.

When the inspection system 10 operates in a non-interlaced mode, the mechanical stage 60 is configured to move at a second speed that differs from the first speed thereby introducing a substantial overlap between scan lines of different beams that are obtained during different scan iterations.

In a non-interlaced mode of operation each point of the sample (or each point of a selected area of the sampled) may be covered by each one of the different beams.

During each one of the operation modes, the detection module 40 is configured to generate detection signals in response to a detection of radiation emitted from the sample as a result of each scan line, and the processor 80 is configured to independently process detection signals relating to different scan lines.

Figure 2:
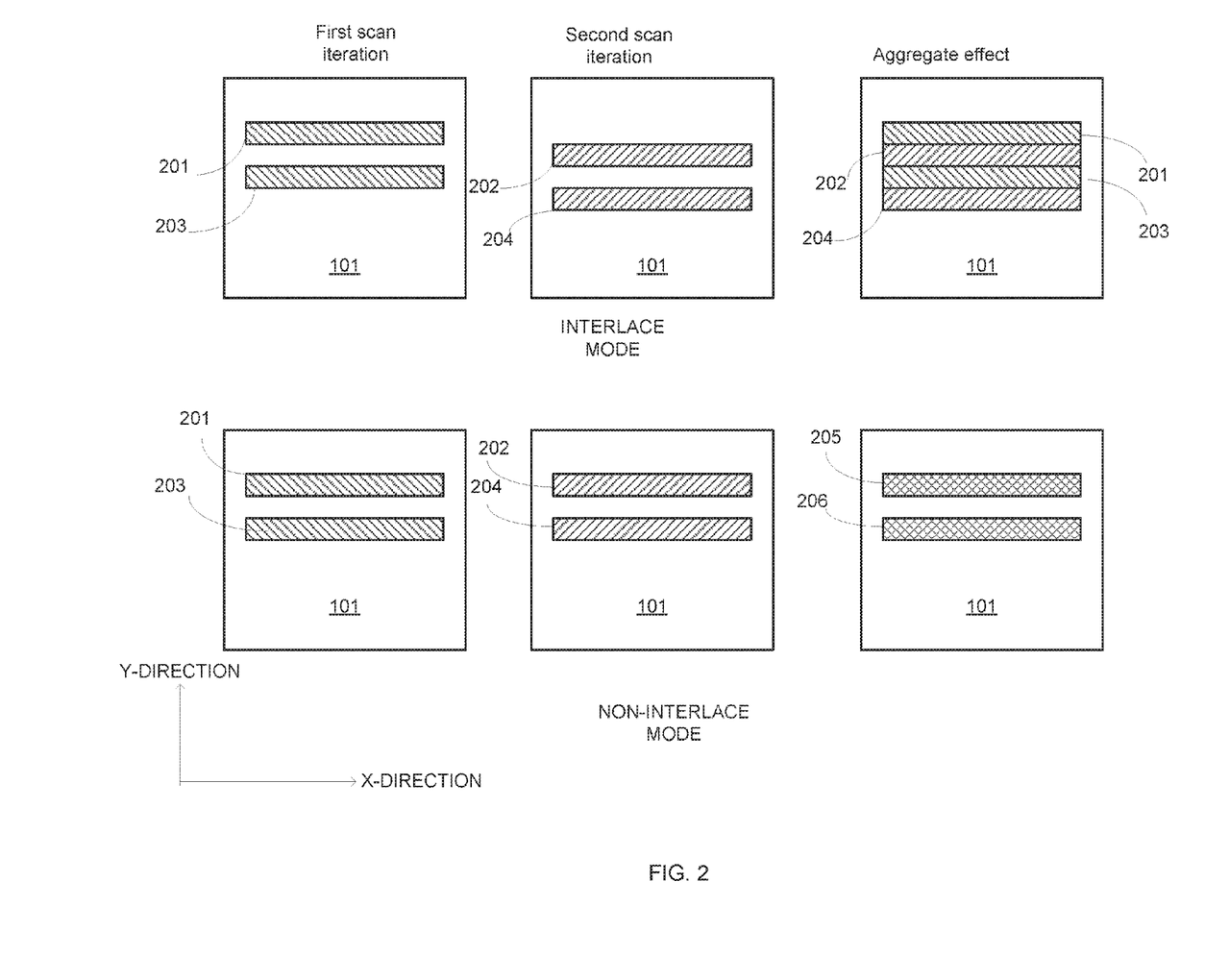
FIG. 2 illustrates scan lines according to an embodiment of the invention.

FIG. 2 illustrates scan lines during a non-interlaced mode and an interlaced mode according to an embodiment of the invention.

During a first scan iteration, beams 71 and 72 scan region 101 of sample 100 by scan lines 201 and 203.

During a second scan iteration, beams 71 and 72 scan region 101 of sample 100 by scan lines 202 and 202.

When operating in the interlaced mode, scan lines 201, 202, 203 and 204 do not substantially overlap but cover a continuous area of scan region 101.

When operating in the non-interlaced mode, scan lines 201, 203 cover the same area (denoted 205 and 206) as scan lines 202 and 204.

Referring back to FIG. 1, the Illumination module 91 is illustrates as including a light source 22 for directing a light beam towards scanner and splitter 24 that splits the light beam to two light beams 701 and 702 (or to more than two light beams) and directs the two light beams toward relay lens 26 that is followed by relay lens 28. Beams 701 and 702 propagate through various optical components of the illumination module and become light beams 71 and 72.

The scanner and splitter 24 may split the light beam 70 to two light beams 701 and 702 without substantially changing the cross section of the light beam—so that light beams 701 and 702 are virtually duplicates of light beam 70.

Relay lens 28 directs the pair of beams through an aperture stop (pupil) 30 towards relay lens 32 and relay lens 34.

Relay lens 34 directs the pair of beams towards beam splitter 36. The two beams pass through beam splitter 36 and towards objective lens 38 that focuses the two beams 71 and 72 on sample 100. Beams 71 and 72 are spaced apart from each when impinging on sample 100.

Each scan line is obtained by scanning the pair of spaced apart beams along the X-direction.

In addition to this "optical" scanning, the sample 100 is moved by the mechanical stage 60 in a Y-direction that may be oriented (and even normal) to the plane of the page of FIG. 10.

Scanning of the optical beam along the scan line may have a duration of T and the width of the scan line may be Y.

When operating in the interlaced mode, the mechanical stage moves at a first speed V1 that substantially equals Y/T.

When operating in the non-interlaced mode, the mechanical stage moves at a first speed V2 that substantially equals 2Y/T.

The light that is scattered or reflected from the sample 100 is collected by objective lens 38, directed towards beam splitter 36 that reflects these light beams towards first detector 42 and second detector 44 of detection module 40.

The detection signals from the detection module 40 are fed to processor 80.

FIG. 1 illustrates first optical property adjusting unit 52 and second optical property adjusting unit 54.

The first optical property adjusting unit 52 and second optical property adjusting unit 54 are positioned between scanner and splitter 24 and the first pair of relay lenses 26 and 28. It should be noted that the first optical property adjusting unit 52 and the second optical property adjusting unit 54 may be positioned elsewhere within the illumination module 91.

The first optical property adjusting unit 52 and second optical property adjusting unit 54 may change an optical property of one of beams 71 and 72 thereby introducing a difference between an optical property of the first beam 71 and an optical property of the second beam 72.

The optical property may differ from an angle of incidence, may be the angle of incidence. For example—the optical property may include color, polarization or a combination thereof. Thus—the first optical property adjusting unit 52 and second optical property adjusting unit 54 may be color filters, polarizers and/or apertures.

Illuminating the sample 100 with beams of different optical properties may enhance the detection capabilities of the inspection system. Operating in the interlaced mode increases the throughput of the inspection system 10.

According to an embodiment of the invention, when the inspection system 10 operates in an interlaced manner, the first optical property adjusting unit 52 and second optical property adjusting unit 54 may be removed from the system, may be configured not to alter any optical property of the beams or may be configured to introduce the same change in the optical properties of beams 71 and 72.

Figure 3:
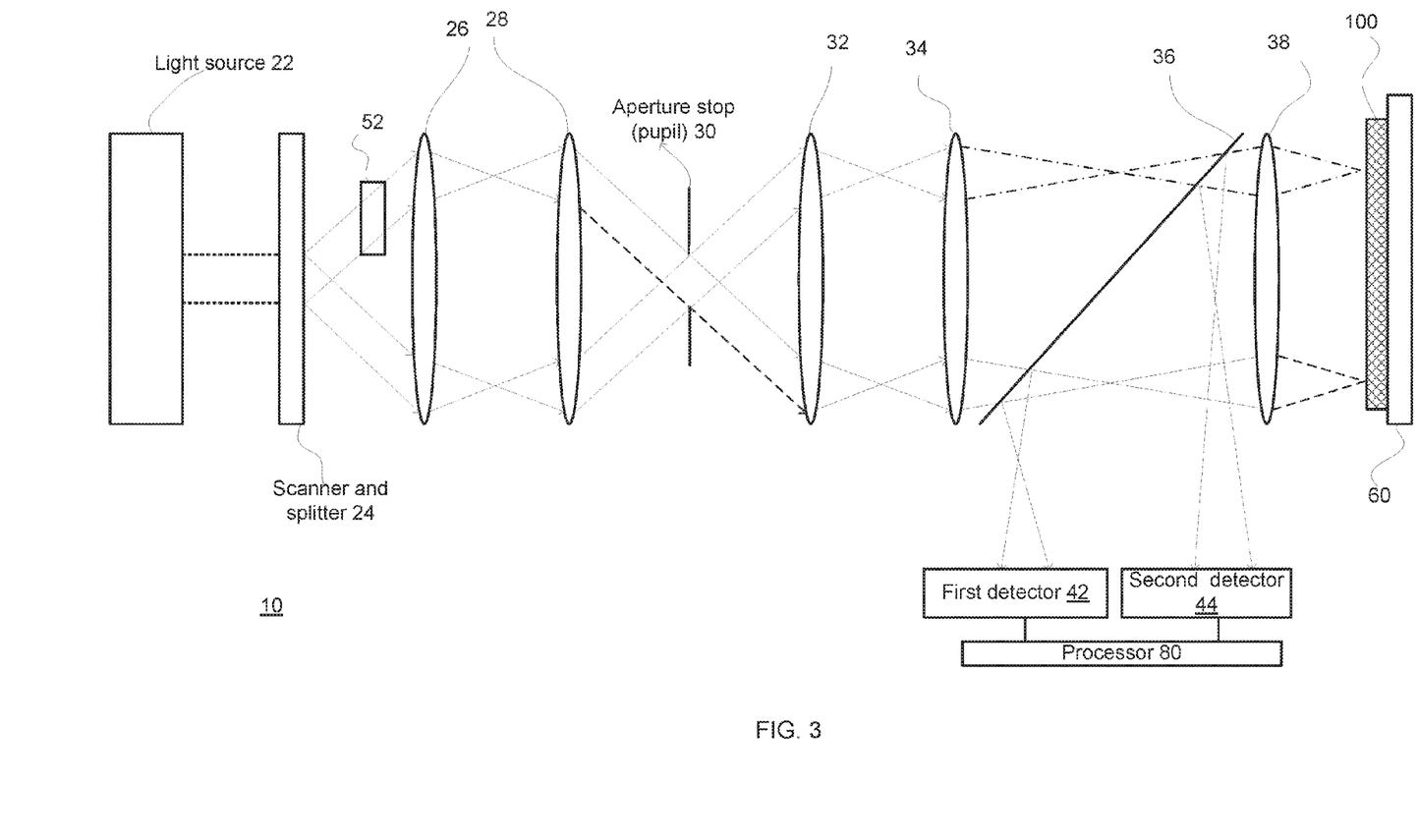
FIG. 3 illustrates a sample and an inspection system according to an embodiment of the invention.

FIG. 3 illustrates inspection system 10 and sample 100 according to an embodiment of the invention.

The inspection system may include a single optical adjusting unit. In FIG. 3 the inspection system 10 is illustrated as including first optical property adjusting unit 52 and not including second optical property adjusting unit 54.

Figure 4:
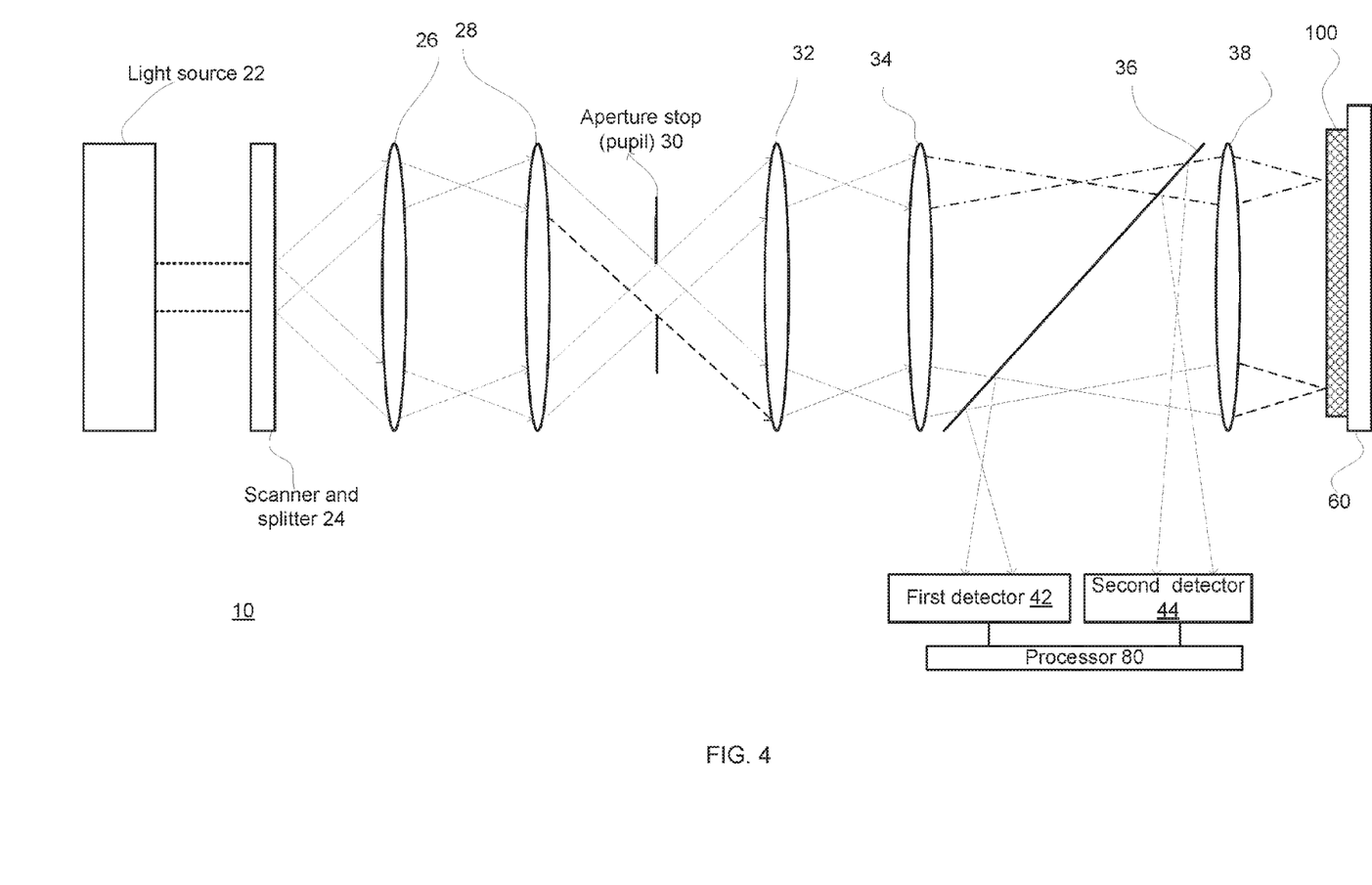
FIG. 4 illustrates a sample and an inspection system according to an embodiment of the invention.

FIG. 4 illustrates inspection system 10 and sample 100 according to an embodiment of the invention. In FIG. 4 inspection system 10 does not include first optical property adjusting unit 52 and does not include second optical property adjusting unit 54.

Figure 5:
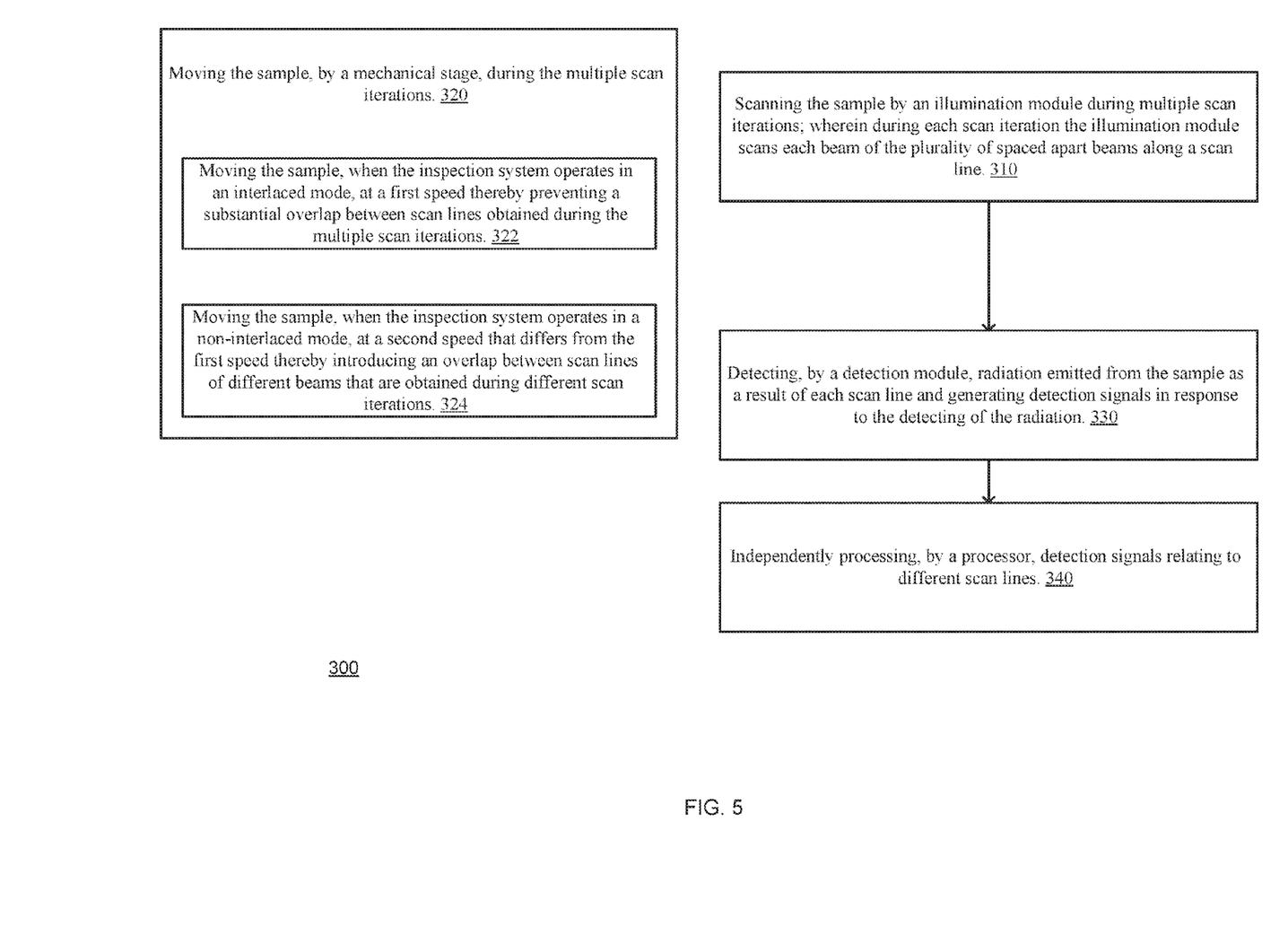
FIG. 5 illustrates a method according to an embodiment of the invention.

FIG. 5 illustrates method 300 for inspecting a sample with a plurality of spaced apart beams, according to an embodiment of the invention.

Method 300 may start by steps 310 and 320.

Step 310 includes scanning the sample by an illumination module during multiple scan iterations; wherein during each scan iteration the illumination module scans each beam of the plurality of spaced apart beams along a scan line.

Step 320 may include moving the sample, by a mechanical stage, during the multiple scan iterations.

Step 320 may include step 322 of moving the sample, when the inspection system operates in an interlaced mode, at a first speed thereby preventing a substantial overlap between scan lines obtained during the multiple scan iterations.

Step 320 may include step 324 of moving the sample, when the inspection system operates in a non-interlaced mode, at a second speed that differs from the first speed thereby introducing an overlap between scan lines of different beams that are obtained during different scan iterations.

Step 310 may be followed by step 330 of detecting, by a detection module, radiation emitted from the sample as a result of each scan line and generating detection signals in response to the detecting of the radiation.

Step 330 may be followed by step 340 of independently processing, by a processor, detection signals relating to different scan lines.

Figure 6:
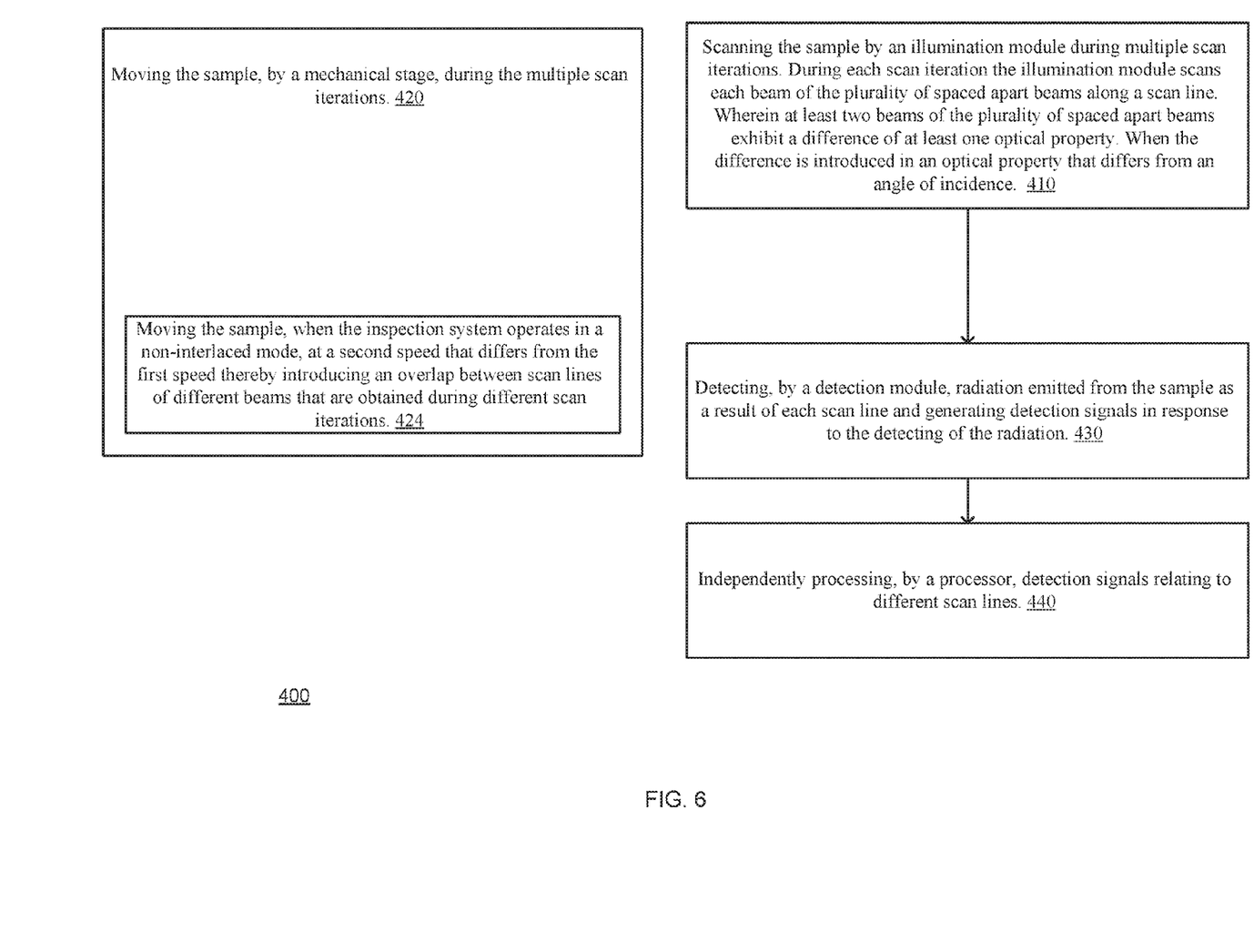
FIG. 6 illustrates a method according to an embodiment of the invention.

FIG. 6 illustrates method 400 for inspecting a sample with a plurality of spaced apart beams, according to an embodiment of the invention.

Method 400 may start by steps 410 and 420.

Step 410 includes scanning the sample by an illumination module during multiple scan iterations. During each scan iteration, the illumination module scans each beam of the plurality of spaced apart beams along a scan line. Wherein at least two beams of the plurality of spaced apart beams exhibit a difference of at least one optical property. When the difference is introduced in an optical property that differs from an angle of incidence.

Step 420 may include moving the sample, by a mechanical stage, during the multiple scan iterations.

Step 410 may be followed by step 430 of detecting, by a detection module, radiation emitted from the sample as a result of each scan line and generating detection signals in response to the detecting of the radiation.

Step 430 may be followed by step 440 of independently processing, by a processor, detection signals relating to different scan lines.

Step 420 may include step 424 of moving the sample, when the inspection system operates in a non-interlaced mode, at a second speed that differs from the first speed thereby introducing an overlap between scan lines of different beams that are obtained during different scan iterations.

Figure 7:
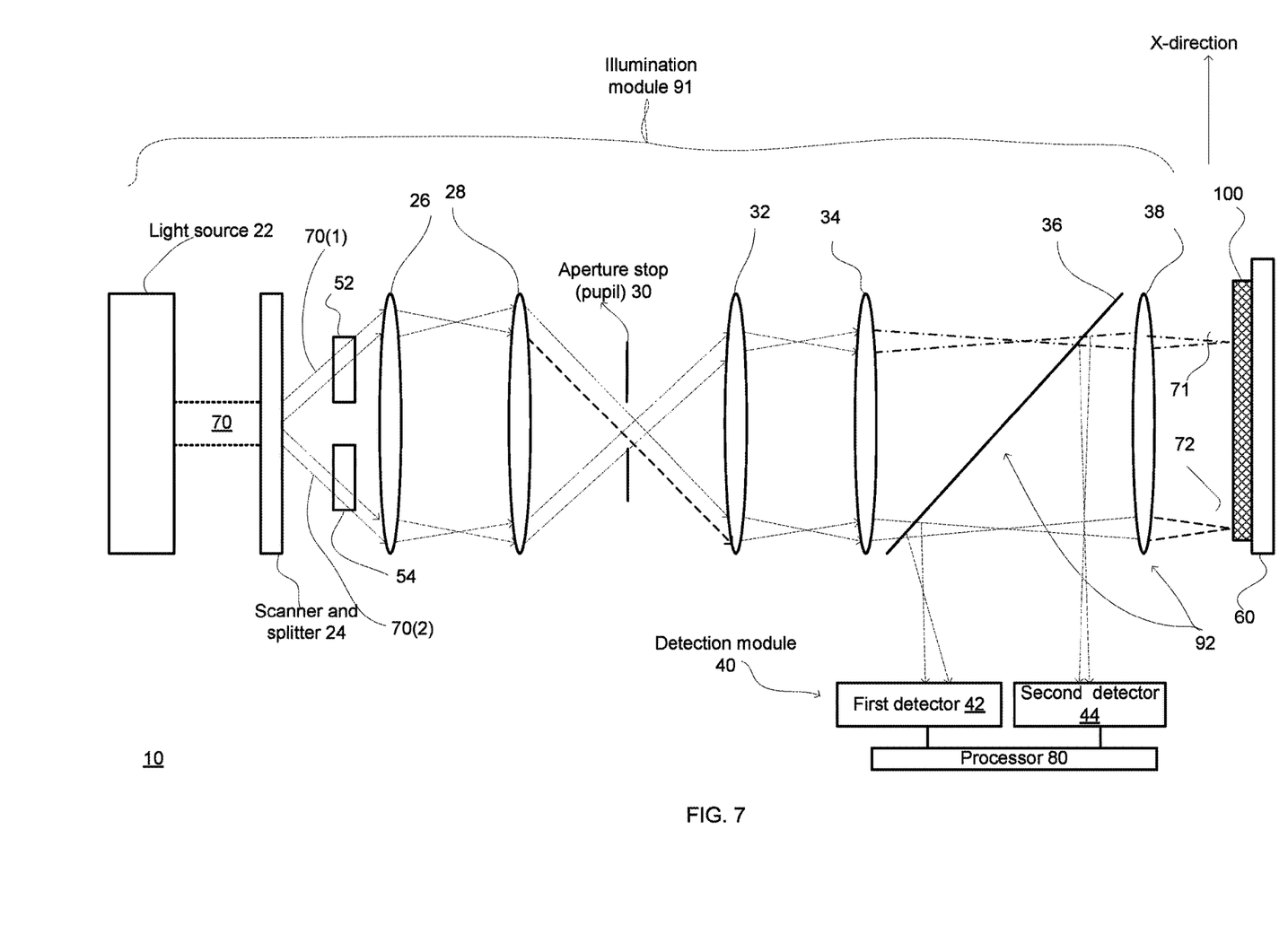
FIG. 7 illustrates a sample and an inspection system according to an embodiment of the invention.

FIG. 7 illustrates sample 100 and an inspection system 10 according to an embodiment of the invention.

The inspection system of FIG. 7 differs from the inspection system of FIG. 1 by having a scanner and splitter 24 that splits the light beam 70 to two light beams 701 and 702 while introducing a substantial change in the cross section of the light beam—so that light beams 701 and 702 have a cross section that is much smaller (for example less than one half) than the cross section of light beam 70.

Figure 8:
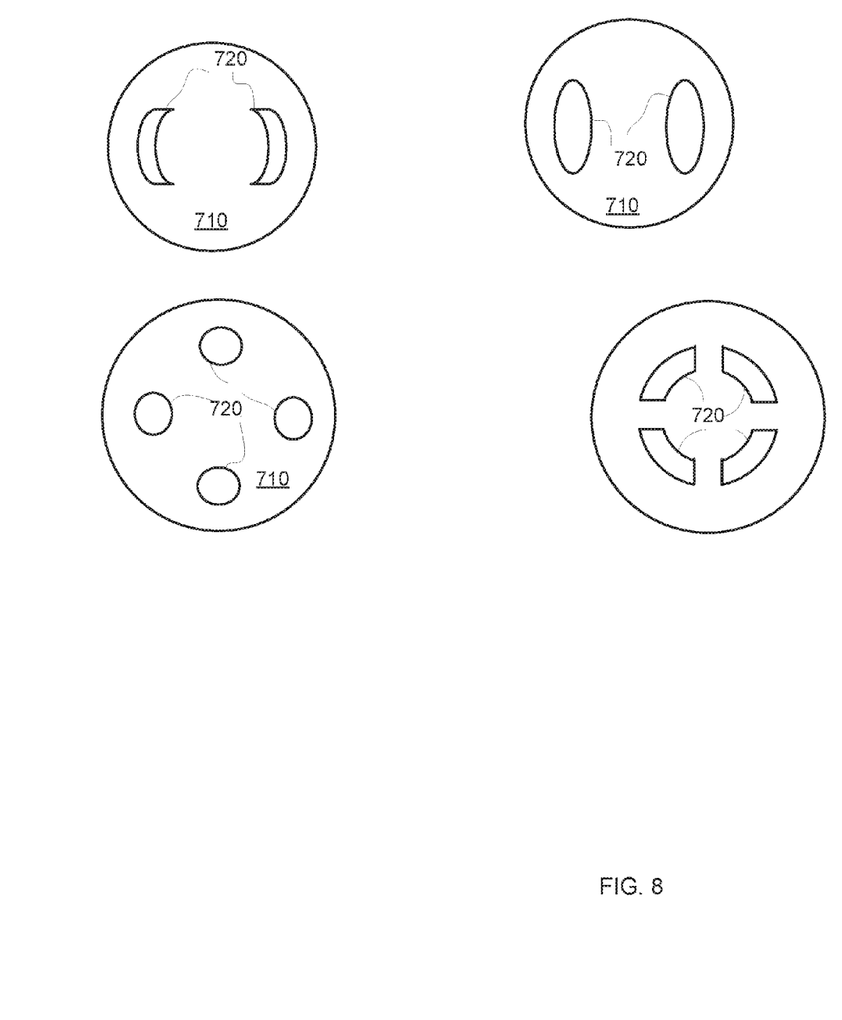
FIG. 8 illustrates various apertures of the inspection system of FIG. 7 according to embodiments of the invention.

The scanner and splitter 24 may have multiple apertures for beam shaping light beams 701 and 702. FIG. 8 illustrates various examples of a apertures 720 that are formed in a disk 710 that belongs to the scanner and splitter. Light beam 70 passes through the apertures to form light beams such as 701 and 702. The number of apertures may exceed two. The apertures may be of the same shape and size and/or may differ by shape and/or size.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of step in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described steps are merely illustrative. The multiple may be combined into a single step, a single step may be distributed in additional steps and steps may be executed at least partially overlapping in time. Moreover, alternative embodiments may include multiple instances of a particular step, and the order of steps may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An inspection system, comprising:
  an illumination module that is configured to scan a sample during multiple scan iterations; wherein during each scan iteration the illumination module scans each beam of a plurality of spaced apart beams along a scan line;
  a mechanical stage that is configured to move the sample during the multiple scan iterations;
  a detection module; and a processor;

wherein when the inspection system operates in an interlaced mode the mechanical stage is configured to move at a first speed thereby preventing a substantial overlap between scan lines obtained during the multiple scan iterations;

wherein when the inspection system operates in a non-interlaced mode:

the mechanical stage is configured to move at a second speed that differs from the first speed thereby introducing an overlap between scan lines of different beams that are obtained during different scan iterations;

the detection module is configured to generate detection signals in response to a detection of radiation emitted from the sample as a result of each scan line; and wherein the processor is configured to independently process detection signals relating to different scan lines.

2. The inspection system according to claim 1, wherein when the inspection system operates in the non-interlaced mode, the illumination module is configured to introduce a difference between at least one optical property of at least two of the plurality of spaced apart beams.

3. The inspection system according to claim 2 wherein the at least one optical property differs from an angle of incidence of the at least two of the plurality of spaced apart beams.

4. The inspection system according to claim 2 wherein the at least one optical property is a polarization of the at least two of the plurality of spaced apart beams.

5. The inspection system according to claim 1 wherein the illumination module comprises a scanner and beam splitter for generating the plurality of spaced apart beams and for scanning the plurality of spaced apart beams.

6. The inspection system according to claim 1 wherein the illumination module comprises a first pair of relay lenses followed by an aperture stop; and wherein the aperture stop is followed by three relay lenses and a beam splitter.

7. An inspection system, comprising:

an illumination module that is configured to scan a sample during multiple scan iterations; wherein during each scan iteration the illumination module scans each beam of a plurality of spaced apart beams along a scan line;

a mechanical stage that is configured to move the sample during the multiple scan iterations;

a detection module; and a processor;

wherein when the inspection system operates in a non-interlaced mode:

the mechanical stage is configured to move the sample and introduce an overlap between scan lines of different beams that are obtained during different scan iterations;

the illumination module is configured to introduce a difference between at least one optical property of at least two of the plurality of spaced apart beams; wherein the at least one optical property differs from an angle of incidence on the sample;

the detection module is configured to generate detection signals in response to a detection of radiation emitted from the sample as a result of each scan line; and wherein the processor is configured to independently process detection signals relating to different scan lines.

8. The inspection system according to claim 7 wherein the at least one optical property is a polarization of the at least two of the plurality of spaced apart beams.

9. The inspection system according to claim 7 wherein the at least one optical property differs from an angle of incidence of the at least two of the plurality of spaced apart beams.

10. The inspection system according to claim 7 wherein the illumination module comprises a scanner and beam splitter for generating the plurality of spaced apart beams and for scanning the plurality of spaced apart beams.

11. The inspection system according to claim 7 wherein the illumination module comprises a first pair of relay lenses followed by an aperture stop; and wherein the aperture stop is followed by three relay lenses and a beam splitter.

12. A method for inspecting a sample with a plurality of spaced apart beams, the method comprising:

scanning the sample by an illumination module of an inspection system during multiple scan iterations; wherein during each scan iteration the illumination module scans each beam of the plurality of spaced apart beams along a scan line;

moving the sample, by a mechanical stage of the inspection system, during the multiple scan iterations;

detecting, by a detection module of the inspection system, radiation emitted from the sample as a result of each scan line and generating detection signals in response to the detecting of the radiation; and independently processing, by a processor of the inspection system, detection signals relating to different scan lines;

wherein when the inspection system operates in an interlaced mode, the moving of the sample is done at a first speed thereby preventing a substantial overlap between scan lines obtained during the multiple scan iterations; and wherein when the inspection system operates in a non-interlaced mode, the moving of the sample is done at a second speed that differs from the first speed thereby introducing an overlap between scan lines of different beams that are obtained during different scan iterations.

* * * * *